(12) United States Patent
Chen et al.

(10) Patent No.: US 10,246,437 B2
(45) Date of Patent: Apr. 2, 2019

(54) CRYSTAL FORM OF NERATINIB MALEATE AND PREPARATION METHOD THEREFOR

(71) Applicant: CRYSTAL PHARMATECH CO., LTD, Suzhou, Jiangsu (CN)

(72) Inventors: Minhua Chen, Jiangsu (CN); Yanfeng Zhang, Suzhou (CN); Xiaojuan Diao, Suzhou (CN); Xiaoyu Zhang, Suzhou (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 15/542,597

(22) PCT Filed: Jan. 8, 2016

(86) PCT No.: PCT/CN2016/070472
§ 371 (c)(1),
(2) Date: Jul. 10, 2017

(87) PCT Pub. No.: WO2016/110270
PCT Pub. Date: Jul. 14, 2016

(65) Prior Publication Data
US 2018/0265495 A1     Sep. 20, 2018

(30) Foreign Application Priority Data
Jan. 9, 2015  (CN) .......................... 2015 1 0012580

(51) Int. Cl.
| C07D 401/12 | (2006.01) |
| A61K 31/4709 | (2006.01) |
| C07C 51/41 | (2006.01) |
| C07C 51/43 | (2006.01) |
| C07C 57/145 | (2006.01) |

(52) U.S. Cl.
CPC ........ *C07D 401/12* (2013.01); *A61K 31/4709* (2013.01); *C07C 51/412* (2013.01); *C07C 51/43* (2013.01); *C07C 57/145* (2013.01); *C07B 2200/13* (2013.01)

(58) Field of Classification Search
CPC .............. C07D 401/12; A61K 31/4709; C07C 51/412; C07C 51/43; C07C 57/145; C07B 2200/13
See application file for complete search history.

(56) References Cited

U.S. PATENT DOCUMENTS

| 8,173,814 | B2 * | 5/2012 | Lu ........................ | C07D 401/12 |
| | | | | 546/160 |
| 8,394,959 | B2 * | 3/2013 | Lu ........................ | C07D 401/12 |
| | | | | 546/159 |
| 9,139,558 | B2 * | 9/2015 | Lu ........................ | C07D 401/12 |
| 9,630,946 | B2 * | 4/2017 | Lu ........................ | C07D 401/12 |
| 2006/0270668 | A1 | 11/2006 | Wyeth | |
| 2006/0270669 | A1 | 11/2006 | Wyeth | |
| 2009/0176827 | A1 | 7/2009 | Wyeth | |

FOREIGN PATENT DOCUMENTS

| JP | 2011500712 A | 1/2011 |
| WO | 2009052264 A2 | 4/2009 |

OTHER PUBLICATIONS

Takatany et al., API form screening and selection in drug discovery stage, Pharm Stage, pp. 20-25, vol. 6, No. 10, 2007.
Hirayama Noriaki, Handbook of organic compound crystal preparation: Principle and know-how; Date of publication: Jul. 15, 2008; pp. 57-84.
Mino R. Caira, Crystalline Polymorphism of Organic Compounds, Topics in Cureent Chemistry, vol. 198, pp. 163-208.
C.G. Wermuth, The Practice of Medicinal Chemistry, vol. 2, Technomics Inc, Japan, Sep. 25th, 1999, pp. 347-365.

* cited by examiner

*Primary Examiner* — D Margaret M Seaman
(74) *Attorney, Agent, or Firm* — VLP Law Group LLP; Kent H. Cheng (57) ABSTRACT

The present invention relates to novel crystalline forms of Neratinib maleate and the preparation method thereof. The novel crystalline forms of Neratinib maleate in the present invention have high solubility, good stability, good processability, easy post-treatment process and other favorable properties. The preparation method is simple, low cost, and has an important value for future optimization and development of the drug.

25 Claims, 10 Drawing Sheets

CRYSTAL FORM OF NERATINIB MALEATE AND PREPARATION METHOD THEREFOR

TECHNICAL FIELD

The present invention relates to the field of pharmaceutical chemistry, particularly relates to novel crystalline forms of (2E)-N-[4-[[3-chloro-4-[(pyridin-2-yl)methoxy]phenyl]amino]-3-cyano-7-ethoxyquinolin-6-yl]-4-(dimethylamino)but-2-enamide maleate and process of preparation thereof.

BACKGROUND OF THE INVENTION

Neratinib is an anti-breast cancer drug developed by Wyeth (Pfizer), and then produced by Puma Biotechnology who gets the development rights from Pfizer. It is an oral, irreversible pan-ErbB receptor tyrosine kinase inhibitor, and it can effectively inhibit the activity of ErbB1 and ErbB2 tyrosine kinase. The chemical name of Neratinib is: (2E)-N-[4-[[3-chloro-4-[(pyridin-2-yl)methoxy]phenyl]amino]-3-cyano-7-ethoxyquinolin-6-yl]-4-(d imethylamino)but-2-enamide, and the structure is shown as Formula (I):

(I)

At present, CN101918390B disclosed several salts of Formula (I), including maleate, fumarate, mesylate, p-tosylate, succinate, sulfate, tartrate, and citrate. Physical and chemical properties of these salts were evaluated in the patent, wherein maleate salt exhibited the best physical and chemical properties. However, CN101918390B disclosed only three crystalline forms of maleate, among which Form III is a partly hydrate (a mixture of Form I and Form II); Form I is an anhydrate but can easily convert to Form II by absorbing moisture in the air. So Form I is not suitable for long-term storage. Only Form II can be used for commercial production. Therefore, it is necessary to develop novel crystalline forms which have good stability and higher solubility than maleate Form II in CN101918390B.

The present invention develops novel crystalline forms of maleate which have good stability, high solubility, low hygroscopicity, and are suitable for storage and commercial production. The present invention provides more and better choice for the follow-up development of the drug, and meets the development needs of the drug.

SUMMARY OF THE INVENTION

The present invention provides three novel crystalline forms of maleate of the compound of Formula (I) and the process of preparation thereof. The novel crystalline forms of maleate in the present invention are suitable for the drug research and commercial production.

One objective of the present invention is to provide a novel maleate crystalline form of the compound of Formula (I), designated as Form A.

The crystalline Form A of the present invention, wherein the X-ray powder diffraction pattern shows characteristic peaks at 2theta values of 6.9°±0.2°, 13.9°±0.2° and 22.5°±0.2°.

Furthermore, the crystalline Form A of the present invention, wherein the X-ray powder diffraction pattern future shows one or two or three characteristic peaks at 2theta values of 5.1°±0.2°, 11.4°±0.2° and 18.3°±0.2°. Preferably, the crystalline Form A of the present invention, wherein the X-ray powder diffraction pattern further shows characteristic peaks at 2theta values of 5.1°±0.2°, 11.4°±0.2° and 18.3°±0.2°.

Furthermore, the crystalline Form A of the present invention, wherein the X-ray powder diffraction pattern further shows one or two or three characteristic peaks at 2theta values of 13.2°±0.2°, 15.2°±0.2° and 21.6°±0.2°. Preferably, the crystalline Form A of the present invention, wherein the X-ray powder diffraction pattern further shows characteristic peaks at 2theta values of 13.2°±0.2°, 15.2°±0.2° and 21.6°±0.2°.

Figure 1:
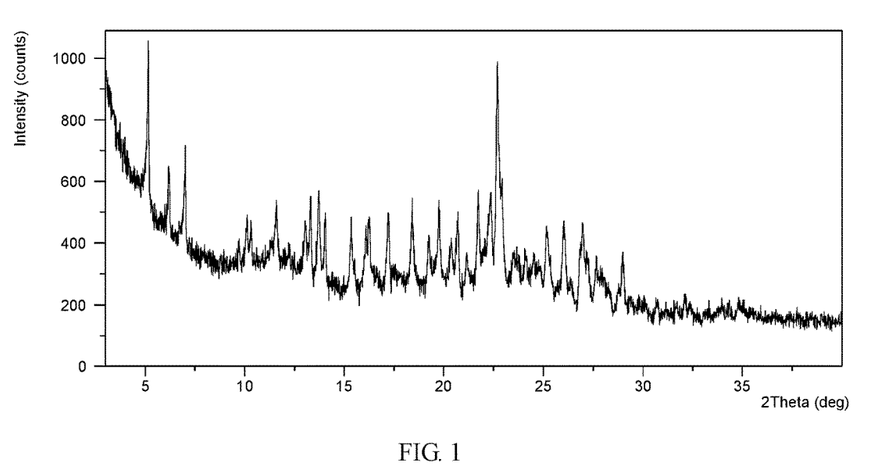
FIG. 1 shows an XRPD pattern of maleate crystalline Form A

Furthermore, the crystalline Form A of the present invention, wherein the X-ray powder diffraction pattern is substantially as depicted in FIG. 1.

Figure 2:
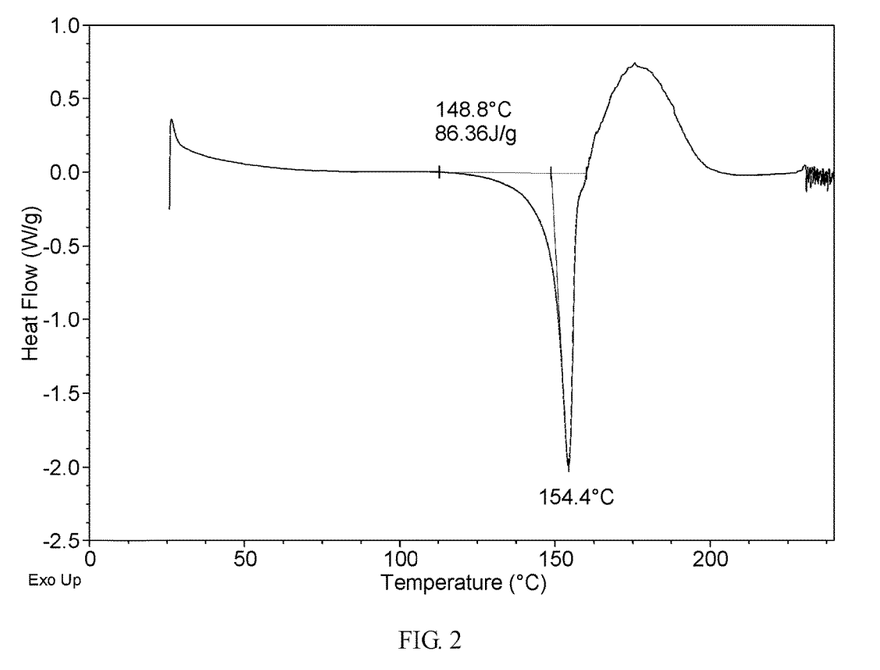
FIG. 2 shows a DSC thermogram of maleate crystalline Form A

The crystalline Form A of the present invention, wherein the differential scanning calorimetry analysis curve (DSC) shows an endothermic peak when heated to about 149° C., and the DSC thermogram is substantially as shown in FIG. 2.

Figure 3:
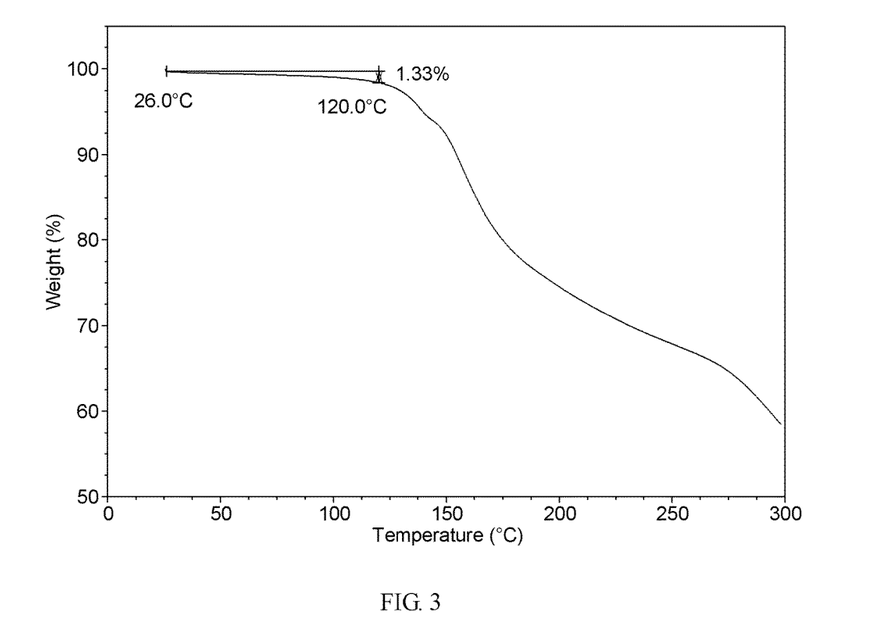
FIG. 3 shows a TGA thermogram of maleate crystalline Form A

The crystalline Form A of the present invention, wherein the thermal gravimetric analysis (TGA) thermogram displayed 1.3% weight loss when heated to 120° C., and the TGA thermogram is substantially as shown in FIG. 3.

The crystalline Form A of the present invention, wherein crystalline Form A is an anhydrate.

Furthermore, the crystalline Form A of the present invention, wherein crystalline Form A is a tri-maleate.

Another objective of the present invention is to provide a process of preparing maleate crystalline Form A, wherein the process comprises: adding the compound of Formula (I) and maleic acid into a single organic solvent or a mixture of several organic solvents, then stirring to get crystals.

Furthermore, these mixed organic solvents are mixed in any ratio.

Furthermore, the organic solvent is selected from ketone solvents, alcohol solvents, aromatic hydrocarbon solvents, halogenated hydrocarbon solvents, nitrile solvents, cyclic ether solvents and C3-C10 alkane solvents.

Furthermore, the organic solvent is selected from acetone, ethanol, isopropanol, toluene, dichloromethane, acetonitrile, tetrahydrofuran and n-heptane.

Furthermore, the molar ratio of the compound of Formula (I) and maleic acid is from 1:2 to 1:5.

Another objective of the present invention is to provide a pharmaceutical composition comprising therapeutically effective amount of maleate crystalline Form A and pharmaceutically acceptable excipients. Generally, mix or contact therapeutically effective amount of crystalline Form A and one or more pharmaceutically acceptable excipients to prepare pharmaceutical composition or formulation, and the pharmaceutical composition or formulation are prepared by well-known method in the pharmaceutical field.

The present invention is directed to the use of maleate crystalline Form A of the compound of Formula (I) for preparing drugs which is used for preventing, treating, or inhibiting cancer, particularly for the treatment of breast cancer.

Another objective of the present invention is to provide another novel crystalline form of maleate of the compound of Formula (I), designated as Form B.

The crystalline Form B of the present invention, wherein the X-ray powder diffraction pattern shows characteristic peaks at 2theta values of 5.4°±0.2°, 13.5°±0.2° and 19.6°±0.2°.

Furthermore, the crystalline Form B of the present invention, wherein the X-ray powder diffraction pattern future shows one or two or three characteristic peaks at 2theta values of 10.7°±0.2°, 12.1°±0.2° and 23.8°±0.2°. Preferably, the crystalline Form B of the present invention, wherein the X-ray powder diffraction pattern further shows characteristic peaks at 2theta values of 10.7°±0.2°, 12.1°±0.2° and 23.8°±0.2°.

Furthermore, the crystalline Form B of the present invention, wherein the X-ray powder diffraction pattern further shows one or two or three characteristic peaks at 2theta values of 9.9°±0.2°, 22.2°±0.2° and 17.6°±0.2°. Preferably, the crystalline Form B of the present invention, wherein the X-ray powder diffraction pattern further shows characteristic peaks at 2theta values of 9.9°±0.2°, 22.2°±0.2° and 17.6°±0.2°.

Figure 4:
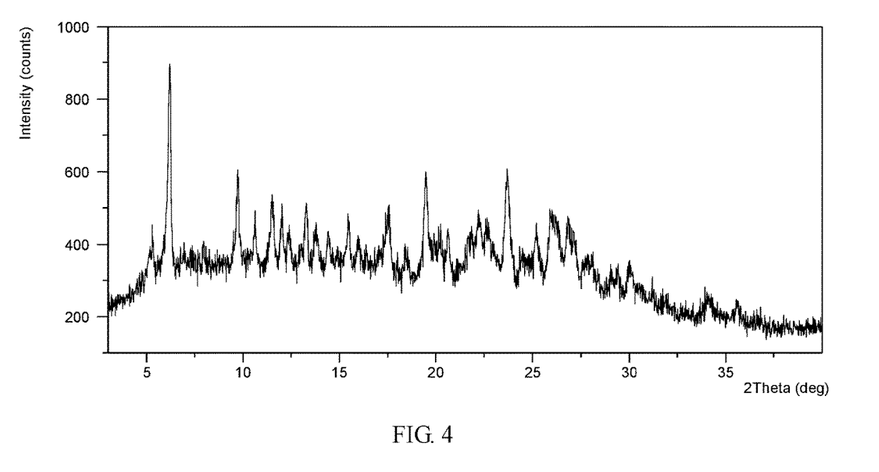
FIG. 4 shows an XRPD pattern of maleate crystalline Form B

Furthermore, the crystalline Form B of the present invention, wherein the X-ray powder diffraction pattern is substantially as shown in FIG. 4.

Figure 5:
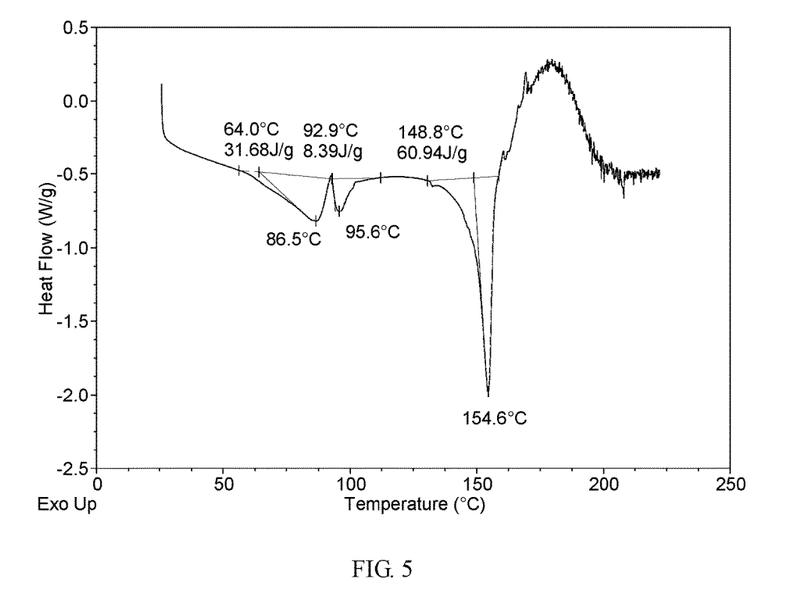
FIG. 5 shows a DSC thermogram of maleate crystalline Form B

The crystalline Form B of the present invention, wherein the differential scanning calorimetry analysis curve (DSC) shows the first endothermic peak when heated to 64° C., the second endothermic peak when heated to about 93° C., and the third endothermic peak when heated to 149° C. The DSC thermogram is substantially as shown in FIG. 5.

Figure 6:
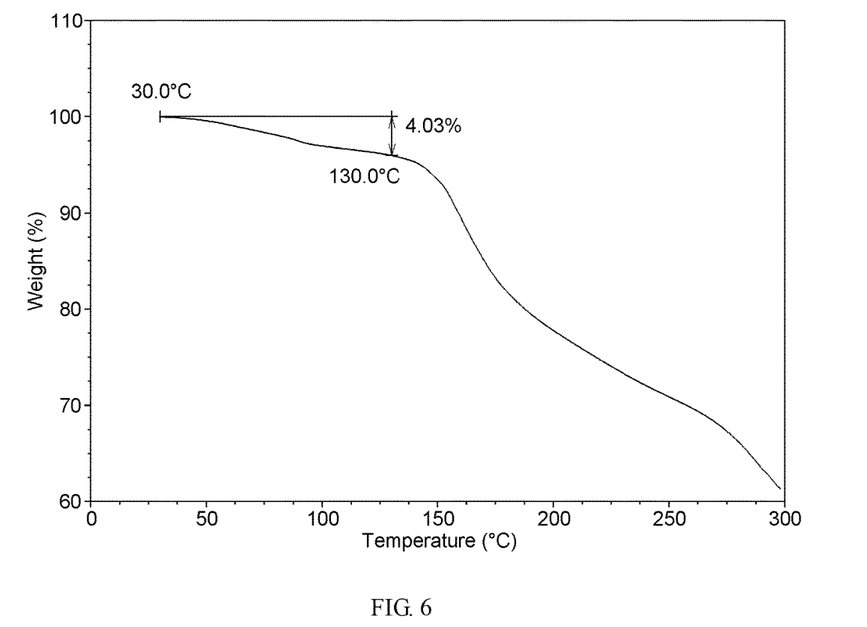
FIG. 6 shows a TGA thermogram of maleate crystalline Form B

The crystalline Form B of the present invention, wherein the thermal gravimetric analysis (TGA) thermogram thereof shows 4.0% weight loss when heated to 130° C., and the TGA thermogram is substantially as shown in FIG. 6.

The crystalline Form B of the present invention, wherein crystalline Form B is a hydrate. Furthermore, the crystalline Form B of the present invention, wherein the maleate salt is a tri-maleate.

Another objective of the present invention is to provide a process of preparing maleate crystalline Form B, wherein the process comprises: stirring maleate crystalline Form A in the present invention in water or a mixture of water and other solvents, or placing maleate crystalline Form A at 60% or above humidity conditions.

Another objective of the present invention is to provide a pharmaceutical composition comprising therapeutically effective amount of maleate crystalline Form B and pharmaceutically acceptable excipients. Generally, mix or contact therapeutically effective amount of crystalline Form B and more pharmaceutically acceptable excipients to make pharmaceutical composition or formulation, and the pharmaceutical composition or formulation are prepared by well-known method in the pharmaceutical field.

The present invention is directed to use of maleate crystalline Form B of the compound of Formula (I) for preparing drugs which is used for preventing, treating, or inhibiting cancer, particularly for the treatment of breast cancer.

Another objective of the present invention is to provide another novel crystalline form of maleate of the compound of Formula (I), designated as Form C.

The crystalline Form C of the present invention, wherein the X-ray powder diffraction pattern shows characteristic peaks at 2theta values of 14.2±0.2°, 15.2°±0.2° and 23.5°±0.2°.

Furthermore, the crystalline Form C of the present invention, wherein the X-ray powder diffraction pattern future shows one or two or three characteristic peaks at 2theta values of 10.9°±0.2°, 21.4°±0.2° and 24.5°±0.2°. Preferably, the crystalline Form C of the present invention, wherein the X-ray powder diffraction pattern further shows characteristic peaks at 2theta values of 10.9°±0.2°, 21.4°±0.2° and 24.5°±0.2°.

Furthermore, the crystalline Form C of the present invention, wherein the X-ray powder diffraction pattern further shows one or two or three characteristic peaks at 2theta values of 23.0°±0.2°, 18.2°±0.2° and 20.3°±0.2°. Preferably, the crystalline Form C of the present invention, wherein the X-ray powder diffraction pattern further shows characteristic peaks at 2theta values of 23.0°±0.2°, 18.2°±0.2° and 20.3°±0.2°.

Figure 7:
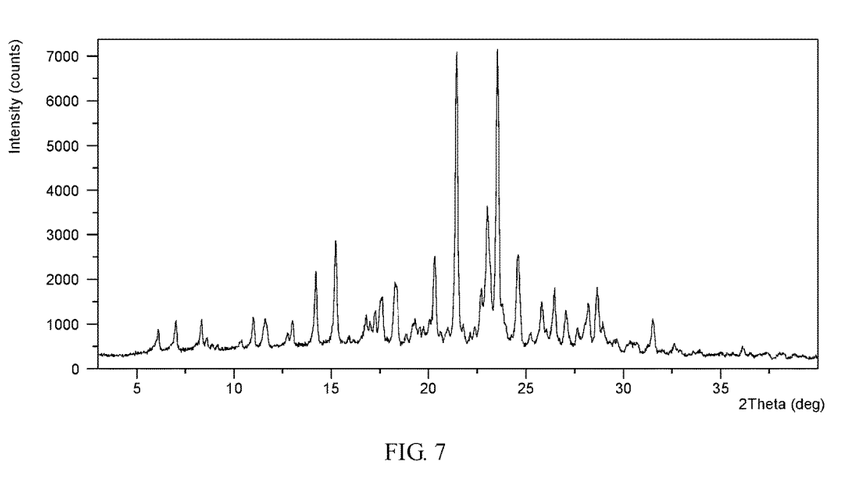
FIG. 7 shows an XRPD pattern of maleate crystalline Form C

Furthermore, the crystalline Form C of the present invention, wherein the X-ray powder diffraction pattern is substantially as shown in FIG. 7.

Figure 8:
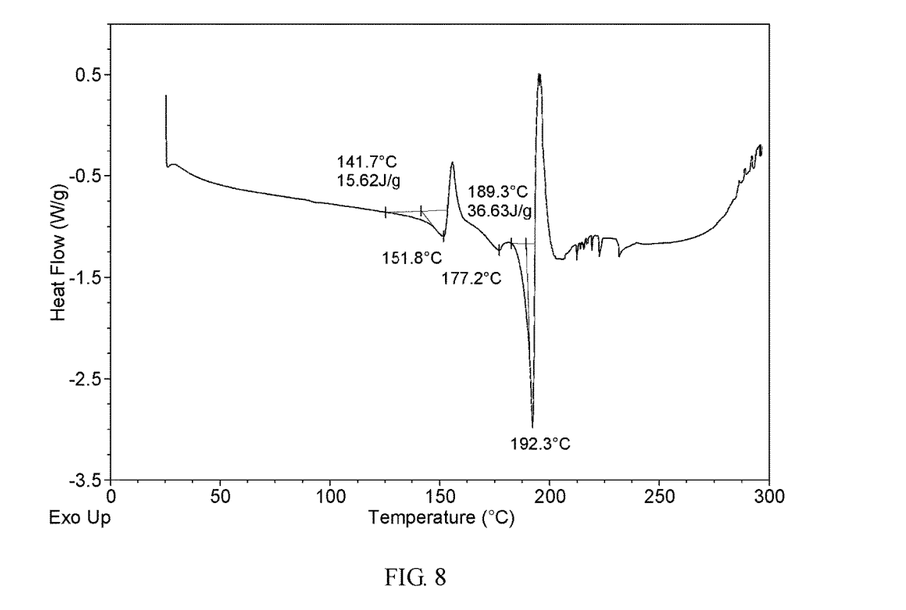
FIG. 8 shows a DSC thermogram of maleate crystalline Form C

The crystalline Form C of the present invention, wherein the differential scanning calorimetry analysis curve (DSC) shows the first endothermic peak when heated to 142° C., the second endothermic peak when heated to 189° C. The DSC thermogram is substantially as shown in FIG. 8.

Figure 9:
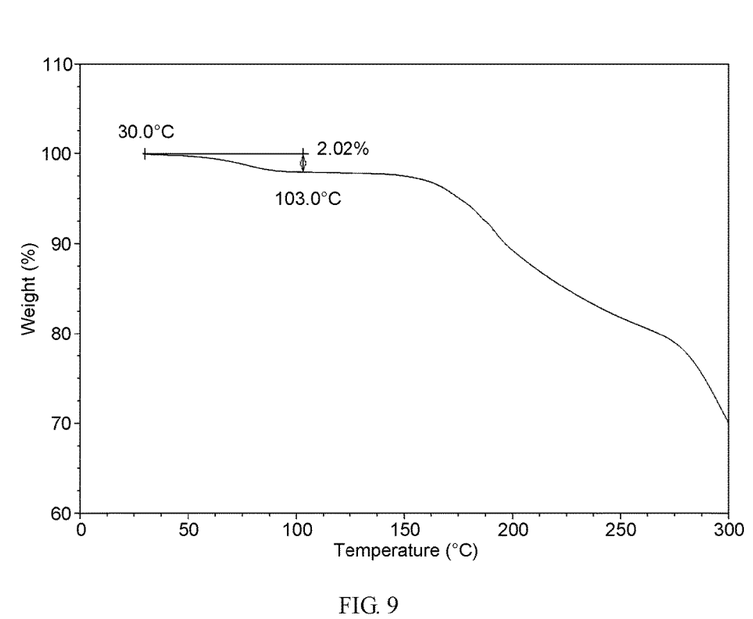
FIG. 9 shows a TGA thermogram of maleate crystalline Form C

The crystalline Form C of the present invention, wherein the thermal gravimetric analysis (TGA) thermogram shows 2.0% weight loss when heated to 103° C., and the TGA thermogram is substantially as shown in FIG. 9.

Furthermore, the crystalline Form C of the present invention, wherein the maleate salt is a mono-maleate.

Another objective of the present invention is to provide a process of preparing maleate crystalline Form C, wherein it comprises: adding the compound of Formula (I) and maleic acid into an single organic solvent or a mixture of several organic solvents, then stirring to get crystals; or stirring amorphous maleate in single organic solvent or a mixture of several organic solvents to get the crystals.

Furthermore, the mixed solvents above are mixed in any ratio.

Furthermore, the organic solvent above is selected from ketone solvents, alcohol solvents, aromatic hydrocarbon solvents, halogenated hydrocarbon solvents, nitrile solvents, cyclic ether solvents, nitro-hydrocarbon and C3-C10 alkane solvents. Furthermore, the organic solvent above is selected from acetone, methanol, toluene, dichloromethane, acetonitrile, tetrahydrofuran, nitromethane and n-heptane.

Furthermore, the molar ratio of the compound of Formula (I) and maleic acid is from 1:1 to 1:1.5.

Another objective of the present invention is to provide a pharmaceutical composition comprising therapeutically effective amount of maleate crystalline Form C and pharmaceutically acceptable excipients. Generally, mix or contact therapeutically effective amount of crystalline Form C and one or more pharmaceutically acceptable excipients to make pharmaceutical composition or formulation, and the pharmaceutical composition or formulation are prepared by well-known method in the pharmaceutical field.

The present invention is directed to use of maleate crystalline Form C of the compound of Formula (I) for preparing drugs which is used for preventing, treating, or inhibiting cancer, particularly for the treatment of breast cancer.

The present invention provides a pharmaceutical composition comprising therapeutically effective amount of crystalline Form A, Form B, Form C or combination thereof and pharmaceutically acceptable excipients. Generally, mix or contact therapeutically effective amount of crystalline Form A, Form B, Form C or the combination thereof and one or more pharmaceutically acceptable excipients to prepare pharmaceutical composition or formulation, and the pharmaceutical composition or formulation are prepared by well-known method in the pharmaceutical field.

The present invention is directed to use of crystalline Form A, Form B, or Form C of maleate of the compound of Formula (I) for preparing drugs which is used for preventing, treating, or inhibiting cancer, particularly for the treatment of breast cancer.

The three novel crystalline forms of maleate of the present invention have good stability, and special condition when drying is not needed in the preparation process, so it simplifies the preparation and post-treatment process of the product. And it is easy for the commercial production.

Comparing with the maleate crystalline Form II in CN101918390B, crystalline Form A and Form B of the present invention have higher solubility and is more suitable for improving bioavailability and efficacy of drug. Comparing with the maleate crystalline Form II in CN101918390B, maleate crystalline Form C of the present invention has better stability and is more suitable for commercial production.

The present invention has the following advantages:

The novel crystalline forms of maleate of the present invention have good stability and can well avoid the occurrence of crystal transition during the drug storage and development, and thus can avoid the change of solubility, dissolution, bioavailability and efficacy of drug, and reduce the possibility of change of efficacy and safety of the polymorphous drugs due to crystal transition.

The novel crystalline forms of maleate of the present invention have higher solubility than polymorphs in prior art, improved dissolution rate of the drug in vivo, and improved bioavailability.

DETAILED DESCRIPTION OF THE INVENTION

The present invention will be further explained by the specific embodiments, but are not intended to limit the scope of the present invention. The skilled in the art can make improvements to the process of preparation and the used instruments within the scope of the claims, and those improvements should be considered as falling into the scope of the present invention. Therefore, the protective scope of the present invention patent should be defined by the claims.

The abbreviations used in the invention are explained as follows:

XRPD: X-ray Powder Diffraction
DSC: Differential Scanning calorimetry
TGA: Thermal Gravimetric Analysis
$^1$HNMR: Proton Nuclear Magnetic Resonance X-ray powder diffraction pattern in the present invention was acquired by a Panalytical Empyrean X-ray powder diffractometer. The parameters of the X-ray powder diffraction method of the present invention were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present invention were acquired by a TA Q2000. The parameters of the differential scanning calorimetry (DSC) method of the present invention were as follow:

Heating rate: 10° C./min
Purge gas: nitrogen.

Thermal gravimetric analysis (TGA) data in the present invention were acquired by a TA Q5000. The parameters of the thermal gravimetric analysis (TGA) method of the present invention were as follow:

Heating rate: 10° C./min;
Purge gas: nitrogen.

EXAMPLE 1

Process of preparing maleate crystalline Form A of the compound of Formula (I):

101.2 mg of compound of Formula (I) was dissolved into 4.0 mL of dichloromethane, and 73.3 mg of maleic acid was added to the solution, then it was stirred at room temperature for 12 hours and centrifuged to give a solid.

$^1$HNMR data of the maleate product prepared by the above process are in the following, and the data indicates that the molar ratio of the compound of the Formula (I) and maleic acid is 1:3, so the maleate above is a tri-maleate.

$^1$HNMR (400 MHz, DMSO-d6) δ 9.81 (s, 1H), 9.76 (s, 1H), 8.95 (s, 1H), 8.60 (d, J=4.1 Hz, 1H), 8.54 (s, 1H), 7.88 (td, J1=7.7 Hz, J2=1.7 Hz, 1H), 7.59 (d, J=7.8 Hz, 1H), 7.37-7.42 (m, 3H), 7.21-7.26 (m, 2H), 6.82-6.70 (m, 2H), 6.20 (s, 6H), 5.29 (s, 2H), 4.33 (q, J=6.9 Hz, 2H), 3.96 (d, J=5.4 Hz, 2H), 2.81 (s, 6H), 1.47 (t, J=6.9 Hz, 3H).

Figure 10:
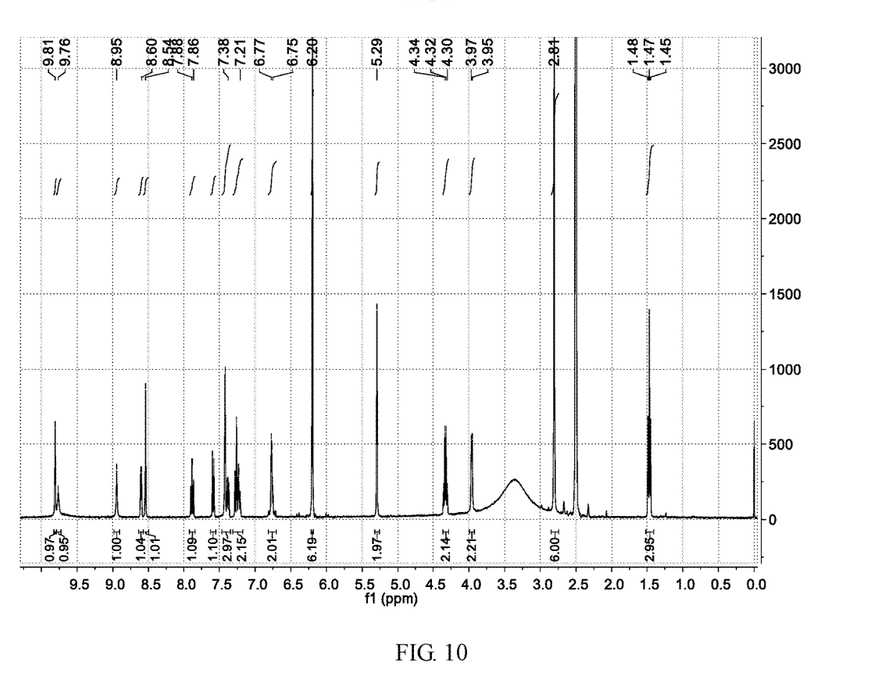
FIG. 10 shows a $^1$HNMR spectrum of maleate crystalline Form A

The XRPD data of the solid prepared in this example are listed in Table 1. The result shows the solid is maleate Form A. The DSC thermogram is displayed in FIG. 2, the TGA thermogram is displayed in FIG. 3 and the $^1$HNMR spectrum is displayed in FIG. 10.

TABLE 1

| 2theta | d spacing | Relative intensity % |
| --- | --- | --- |
| 5.06 | 17.46 | 56.99 |
| 5.71 | 15.48 | 21.57 |
| 6.91 | 12.80 | 34.12 |
| 9.99 | 8.85 | 20.20 |
| 10.18 | 8.69 | 21.33 |
| 11.48 | 7.71 | 6.89 |
| 12.08 | 7.33 | 6.51 |
| 13.18 | 6.72 | 31.12 |
| 13.59 | 6.52 | 21.52 |
| 13.92 | 6.36 | 26.72 |
| 15.21 | 5.82 | 17.24 |
| 16.10 | 5.51 | 19.20 |
| 16.53 | 5.36 | 6.52 |
| 17.06 | 5.20 | 23.19 |
| 17.40 | 5.10 | 11.88 |
| 18.26 | 4.86 | 24.36 |
| 19.13 | 4.64 | 14.07 |
| 19.62 | 4.53 | 11.25 |
| 20.57 | 4.32 | 22.14 |
| 21.00 | 4.23 | 7.65 |
| 21.58 | 4.12 | 24.34 |
| 22.16 | 4.01 | 35.54 |
| 22.54 | 3.94 | 44.81 |
| 23.37 | 3.81 | 7.83 |
| 23.97 | 3.71 | 9.08 |
| 24.65 | 3.61 | 10.67 |
| 25.08 | 3.55 | 13.90 |
| 25.89 | 3.44 | 15.06 |
| 26.76 | 3.33 | 16.89 |
| 27.97 | 3.19 | 100.00 |
| 28.81 | 3.10 | 15.88 |
| 31.90 | 2.81 | 5.94 |

EXAMPLE 2

Process of preparing maleate crystalline Form A of the compound of Formula (I):

19.8 mg of compound of Formula (I) was added into 1.0 mL of acetone to obtain a suspension, and 13.0 mg of maleic acid was added into the suspension, then it was stirred at room temperature for 12 hours and centrifuged to give a solid.

The XRPD data of the solid prepared in this example are listed in Table 2 and the result indicates the solid is maleate crystalline Form A. The XRPD pattern is displayed in FIG. 1.

TABLE 2

| 2theta | d spacing | Relative intensity % |
| --- | --- | --- |
| 5.06 | 17.46 | 64.25 |
| 6.09 | 14.51 | 23.98 |
| 6.91 | 12.79 | 43.77 |
| 10.03 | 8.82 | 22.55 |
| 10.22 | 8.66 | 18.39 |
| 11.51 | 7.69 | 28.84 |
| 12.95 | 6.83 | 23.95 |
| 13.21 | 6.70 | 36.42 |
| 13.63 | 6.50 | 39.74 |
| 13.94 | 6.35 | 26.67 |
| 15.25 | 5.81 | 27.56 |
| 16.14 | 5.49 | 28.10 |
| 17.11 | 5.18 | 32.89 |
| 18.31 | 4.85 | 33.71 |
| 19.17 | 4.63 | 23.62 |
| 19.67 | 4.51 | 39.84 |
| 20.29 | 4.38 | 23.73 |
| 20.62 | 4.31 | 32.76 |
| 21.09 | 4.21 | 16.98 |
| 21.64 | 4.11 | 45.43 |
| 22.27 | 3.99 | 44.82 |
| 22.61 | 3.93 | 100.00 |
| 22.86 | 3.89 | 46.94 |
| 23.51 | 3.78 | 18.88 |
| 24.02 | 3.71 | 21.05 |
| 25.09 | 3.55 | 33.16 |
| 25.95 | 3.43 | 33.75 |
| 26.89 | 3.32 | 22.63 |
| 27.56 | 3.24 | 10.94 |
| 28.89 | 3.09 | 35.56 |
| 30.62 | 2.92 | 12.17 |
| 32.04 | 2.79 | 15.72 |

EXAMPLE 3

Process of preparing maleate crystalline Form A of the compound of Formula (I):

10.0 mg of compound of Formula (I) was added into 0.5 mL of isopropanol to obtain a suspension, then 6.0 mg of maleic acid was added into the suspension and 0.6 mL of n-hexane was added drop by drop when stirring, then it was stirred at room temperature for 12 hours and centrifuged to give a solid.

The XRPD data of the solid prepared in this example are listed in Table 3 and the result indicates the solid is maleate crystalline Form A.

TABLE 3

| 2theta | d spacing | Relative intensity % |
| --- | --- | --- |
| 5.06 | 17.46 | 15.35 |
| 6.04 | 14.63 | 100.00 |
| 6.84 | 12.92 | 28.14 |
| 9.57 | 9.25 | 26.21 |
| 11.38 | 7.78 | 40.16 |
| 12.25 | 7.23 | 20.00 |
| 13.12 | 6.75 | 47.16 |
| 13.86 | 6.39 | 24.84 |
| 15.23 | 5.82 | 21.12 |
| 15.90 | 5.57 | 18.03 |
| 17.32 | 5.12 | 21.34 |
| 18.19 | 4.88 | 18.73 |
| 19.33 | 4.59 | 27.89 |
| 20.16 | 4.40 | 24.13 |
| 21.54 | 4.13 | 27.97 |
| 22.10 | 4.02 | 45.25 |
| 22.51 | 3.95 | 39.73 |
| 23.48 | 3.79 | 27.07 |
| 25.03 | 3.56 | 24.17 |
| 26.05 | 3.42 | 28.90 |
| 27.83 | 3.21 | 17.59 |

TABLE 3-continued

| 2theta | d spacing | Relative intensity % |
|---|---|---|
| 28.75 | 3.10 | 14.77 |
| 29.86 | 2.99 | 10.84 |
| 33.89 | 2.65 | 4.38 |

EXAMPLE 4

Process of preparing maleate crystalline Form B of the compound of Formula (I):

93.2 mg of crystalline Form A prepared in example 1 was added into 2.0 mL of water to obtain a suspension, then it was stirred at room temperature for 2 hours and centrifuged to give a solid.

$^1$HNMR data of the maleate product prepared by the above method are in the following, and the data indicates the molar rate of the compound of Formula (I) and maleic acid is 1:3, so the maleate salt above is a tri-maleate.

$^1$HNMR (400 MHz, DMSO-d6) δ 9.81 (s, 1H), 9.78 (s, 1H), 8.95 (s, 1H), 8.60 (d, J=4.1 Hz, 1H), 8.55 (s, 1H), 7.88 (td, J1=7.7 Hz, J2=1.7 Hz, 1H), 7.59 (d, J=7.8 Hz, 1H), 7.47-7.34 (m, 3H), 7.21-7.28 (m, 2H), 6.88-6.65 (m, 2H), 6.19 (s, 6H), 5.30 (s, 2H), 4.33 (q, J=6.9 Hz, 2H), 3.96 (d, J=5.3 Hz, 2H), 2.81 (s, 6H), 1.47 (t, J=6.9 Hz, 3H).

Figure 11:
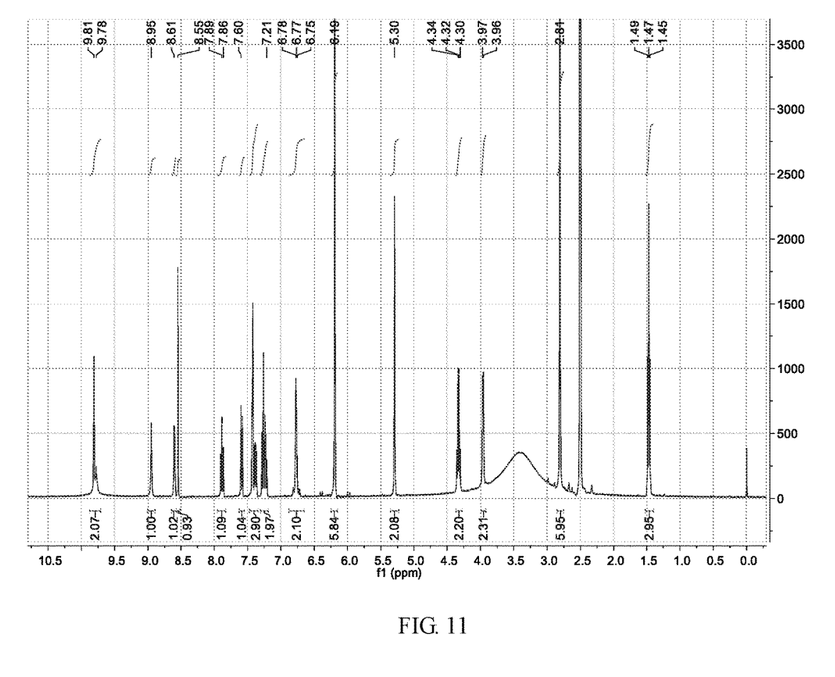
FIG. 11 shows a $^1$HNMR spectrum of maleate crystalline Form B

The XRPD data of the solid produced in this example are listed in Table 4. The result indicates the solid is maleate crystalline Form B. The DSC thermogram is displayed in FIG. 5, the TGA thermogram is displayed in FIG. 6 and the $^1$HNMR spectrummm is displayed in FIG. 11.

TABLE 4

| 2theta | d spacing | Relative intensity % |
|---|---|---|
| 5.41 | 16.34 | 55.81 |
| 6.23 | 14.20 | 33.26 |
| 8.01 | 11.04 | 27.69 |
| 9.85 | 8.98 | 81.55 |
| 10.72 | 8.26 | 47.20 |
| 12.14 | 7.29 | 69.13 |
| 13.47 | 6.57 | 100.00 |
| 14.55 | 6.09 | 43.14 |
| 16.09 | 5.51 | 50.92 |
| 17.58 | 5.05 | 52.81 |
| 19.60 | 4.53 | 95.16 |
| 22.20 | 4.00 | 55.36 |
| 23.84 | 3.73 | 56.71 |
| 26.10 | 3.41 | 36.73 |
| 27.57 | 3.24 | 25.35 |
| 29.24 | 3.05 | 23.21 |
| 30.15 | 2.96 | 18.92 |

EXAMPLE 5

Process of preparing maleate crystalline Form B of the compound of Formula (I):

9.91 mg of crystalline Form A prepared in example 1 was stored at 95% RH for 12 hours, then the solid was collected.

The XRPD data of solid prepared in this example are listed in Table 5 and the result indicates the solid is maleate crystalline Form B.

The XRPD pattern is displayed in FIG. 4.

TABLE 5

| 2theta | d spacing | Relative intensity % |
|---|---|---|
| 5.41 | 16.34 | 17.24 |
| 6.34 | 13.93 | 100.00 |
| 9.88 | 8.95 | 40.52 |
| 10.77 | 8.21 | 21.45 |
| 11.67 | 7.58 | 31.40 |
| 12.16 | 7.28 | 24.55 |
| 13.43 | 6.59 | 31.85 |
| 13.93 | 6.36 | 22.47 |
| 14.58 | 6.07 | 17.93 |
| 15.62 | 5.68 | 25.91 |
| 16.12 | 5.50 | 16.52 |
| 17.67 | 5.02 | 31.29 |
| 18.59 | 4.77 | 12.88 |
| 19.64 | 4.52 | 51.09 |
| 20.79 | 4.27 | 25.00 |
| 22.39 | 3.97 | 32.87 |
| 23.84 | 3.73 | 54.56 |
| 25.35 | 3.51 | 28.18 |
| 26.16 | 3.41 | 36.66 |
| 27.00 | 3.30 | 33.61 |
| 28.05 | 3.18 | 16.72 |
| 29.40 | 3.04 | 9.74 |
| 30.19 | 2.96 | 16.29 |
| 34.27 | 2.62 | 8.54 |
| 35.75 | 2.51 | 7.23 |

EXAMPLE 6

Stability assessment of maleate crystalline Form B of the compound of Formula (I)

Figure 13:
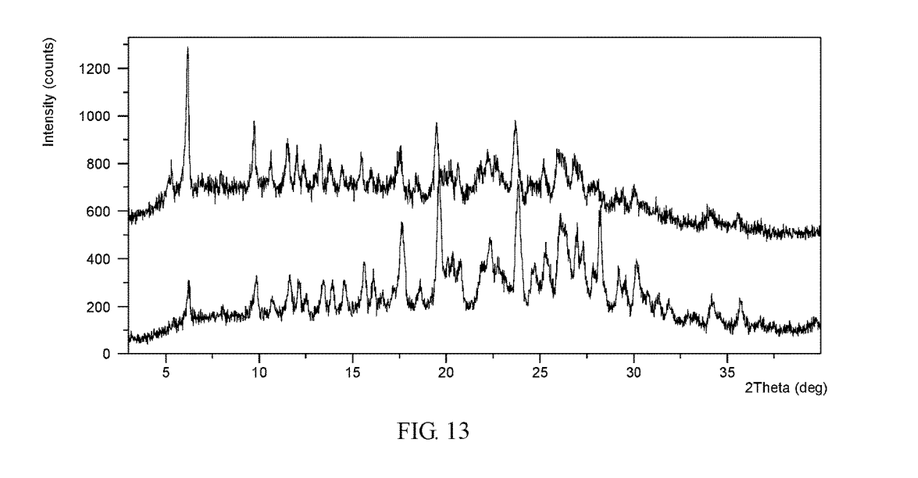
FIG. 13 shows an XRPD overlay pattern of maleate crystalline Form B before and after storing at 5° C. for 90 days (the pattern above is before storing and the below one is after storing)
Figure 14:
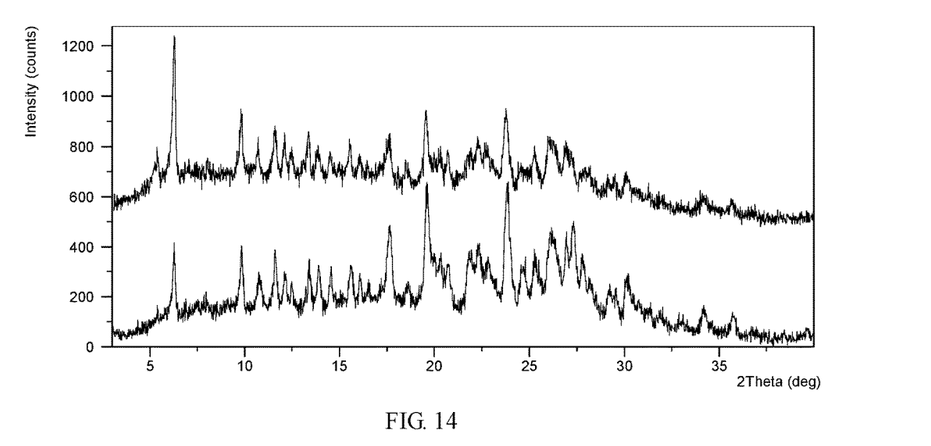
FIG. 14 shows an XRPD overlay pattern of maleate crystalline Form B before and after storing at 25° C./60% RH for 90 days (the pattern above is before storing and the below one is after storing)
Figure 15:
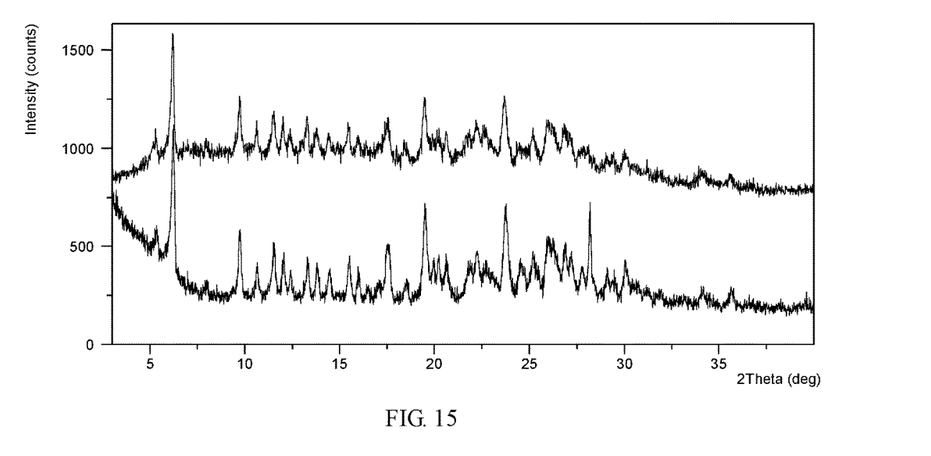
FIG. 15 shows an XRPD overlay pattern of maleate crystalline Form B before and after storing at 40° C./75% RH for 90 days (the pattern above is before storing and the below one is after storing)

Form B in the present invention were stored under 5° C., 25° C./60% relative humidity and 40° C./75% RH for 90 days. XRPD patterns were collected after storage. The result of stability assessment is tabulated in Table 6. The XRPD patterns of Form B before and after storing under the three stress conditions are displayed in FIG. 13, FIG. 14 and FIG. 15 (the above patterns of FIG. 13, FIG. 14 and FIG. 15 were the XRPD patterns of Form B before storing).

TABLE 6

| Initial Form | conditions | Storage time | Form Change |
|---|---|---|---|
| Form B | 5° C. | 90 days | Form B doesn't change (FIG. 13 below) |
| | 25° C./60% RH | 90 days | Form B doesn't change (FIG. 14 below) |
| | 40° C./75% RH | 90 days | Form B doesn't change (FIG. 15 below) |

The result indicates that maleate Form B of the compound of Formula (I) remains unchanged after stored at 5° C., 25° C./60% RH and 40° C./75% RH for 90 days. The maleate crystalline Form B of the compound of Formula (I) has good stability.

EXAMPLE 7

Process of preparing maleate crystalline Form C of the compound of Formula (I):

50.0 mg of compound of Formula (I) was dissolved into 2.0 mL of nitromethane, and 12.1 mg of maleic acid was added into the solution, then it was stirred at room temperature for 12 hours and centrifuged to give a solid.

$^1$HNMR data of the maleate product prepared by the above method are in the following, and the data indicates the molar rate of the compound of Formula (I) and maleic acid is 1:1, so the maleate salt above is a mono-maleate.

$^1$HNMR (400 MHz, DMSO-d6) δ 9.79 (s, 1H), 9.66 (s, 1H), 8.93 (s, 1H), 8.60 (d, J=4.2 Hz, 1H), 8.50 (s, 1H), 7.88

(td, J1=7.7 Hz, J2=1.7 Hz, 1H), 7.59 (d, J=7.8 Hz, 1H), 7.45-7.34 (m, 3H), 7.20-7.27 (m, 2H), 6.82-6.69 (m, 2H), 6.05 (s, 2H), 5.29 (s, 2H), 4.33 (q, J=7.1 Hz, 2H), 3.93 (d, J=3.5 Hz, 2H), 2.79 (s, 6H), 1.46 (t, J=7.0 Hz, 3H).

Figure 12:
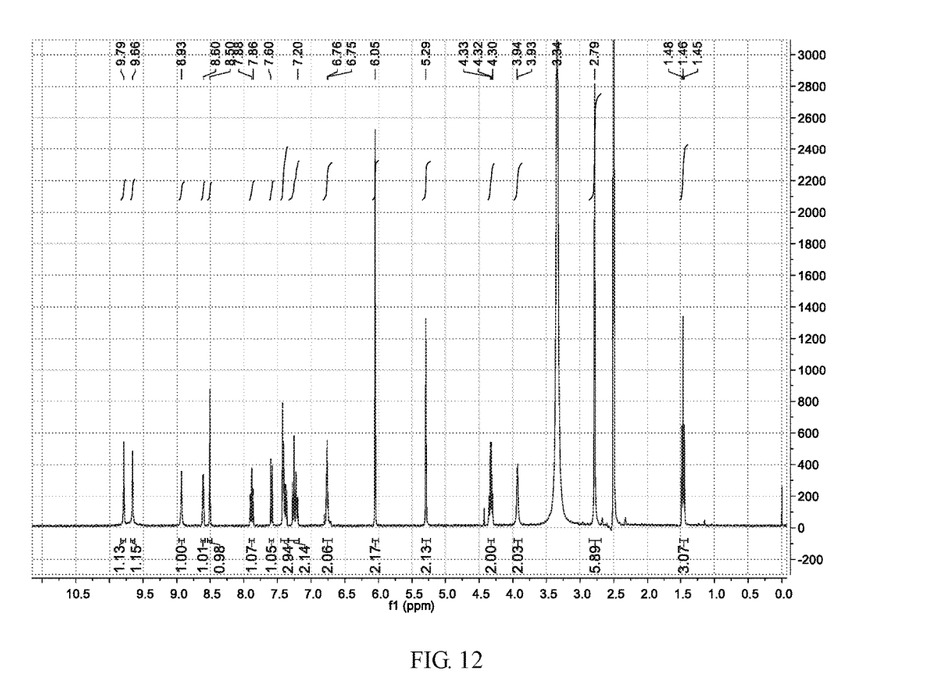
FIG. 12 shows a $^1$HNMR spectrum of maleate crystalline Form C

The XRPD data of the solid prepared in this example are listed in Table 7 and the result indicates the solid is maleate crystalline Form C. The XRPD pattern is displayed in FIG. 7, the DSC thermogram is displayed in FIG. 8, the TGA thermogram is displayed in FIG. 9 and the $^1$HNMR spectrum is displayed in FIG. 12.

TABLE 7

| 2theta | d spacing | Relative intensity % |
|---|---|---|
| 6.05 | 14.62 | 8.32 |
| 6.97 | 12.68 | 10.90 |
| 8.29 | 10.67 | 11.09 |
| 8.56 | 10.33 | 5.69 |
| 8.84 | 10.00 | 3.42 |
| 9.10 | 9.72 | 3.34 |
| 10.31 | 8.58 | 4.50 |
| 10.95 | 8.08 | 12.36 |
| 11.57 | 7.65 | 11.54 |
| 12.71 | 6.97 | 6.80 |
| 12.95 | 6.83 | 11.14 |
| 14.15 | 6.26 | 26.91 |
| 15.17 | 5.84 | 36.86 |
| 15.85 | 5.59 | 6.06 |
| 16.73 | 5.30 | 12.97 |
| 17.19 | 5.16 | 14.19 |
| 17.44 | 5.09 | 16.67 |
| 17.54 | 5.06 | 18.89 |
| 18.23 | 4.87 | 23.35 |
| 18.32 | 4.84 | 21.35 |
| 18.80 | 4.72 | 7.24 |
| 19.25 | 4.61 | 11.69 |
| 20.27 | 4.38 | 32.18 |
| 20.94 | 4.24 | 9.10 |
| 21.39 | 4.15 | 99.31 |
| 21.73 | 4.09 | 10.17 |
| 22.33 | 3.98 | 9.43 |
| 22.66 | 3.92 | 21.15 |
| 22.97 | 3.87 | 48.42 |
| 23.49 | 3.79 | 100.00 |
| 24.54 | 3.63 | 33.10 |
| 25.18 | 3.54 | 7.43 |
| 25.75 | 3.46 | 17.36 |
| 26.41 | 3.37 | 21.97 |
| 27.00 | 3.30 | 14.77 |
| 27.58 | 3.23 | 9.25 |
| 28.15 | 3.17 | 17.15 |
| 28.60 | 3.12 | 22.71 |
| 28.89 | 3.09 | 10.44 |
| 29.61 | 3.02 | 5.31 |
| 30.32 | 2.95 | 4.75 |
| 30.66 | 2.92 | 4.62 |
| 31.48 | 2.84 | 12.30 |
| 32.59 | 2.75 | 4.19 |
| 33.86 | 2.65 | 1.77 |
| 36.10 | 2.49 | 3.06 |
| 37.32 | 2.41 | 1.58 |
| 38.10 | 2.36 | 1.27 |
| 38.74 | 2.32 | 0.97 |

EXAMPLE 8

Process of preparing maleate crystalline Form C of the compound of Formula (I):

Amorphous maleate of compound of Formula (I) was added into 0.2 mL of dichloromethane to obtain a suspension, and it was stirred at room temperature for 48 hours. The suspension was filtered and the wet cake was dried in a vacuum oven at 25° C. overnight to give a solid.

The XRPD data of the solid prepared in this example are listed in Table 8 and the result indicates the solid is maleate crystalline Form C.

TABLE 8

| 2theta | d spacing | Relative intensity % |
|---|---|---|
| 8.55 | 10.34 | 6.73 |
| 10.96 | 8.07 | 15.31 |
| 14.16 | 6.26 | 24.74 |
| 15.19 | 5.83 | 30.21 |
| 16.73 | 5.30 | 6.56 |
| 17.20 | 5.15 | 12.20 |
| 17.51 | 5.06 | 9.00 |
| 18.33 | 4.84 | 12.58 |
| 19.19 | 4.62 | 4.59 |
| 20.29 | 4.38 | 19.47 |
| 21.40 | 4.15 | 100.00 |
| 22.67 | 3.92 | 14.59 |
| 22.98 | 3.87 | 32.96 |
| 23.49 | 3.79 | 68.50 |
| 24.54 | 3.63 | 12.44 |
| 25.77 | 3.46 | 9.47 |
| 26.41 | 3.37 | 20.03 |
| 26.99 | 3.30 | 9.98 |
| 27.59 | 3.23 | 7.87 |
| 28.16 | 3.17 | 9.51 |
| 28.60 | 3.12 | 12.93 |
| 28.86 | 3.09 | 8.66 |
| 31.48 | 2.84 | 6.52 |
| 8.55 | 10.34 | 6.73 |

EXAMPLE 9

Hygroscopicity assessment of maleate Form C of the compound Formula (I)

Figure 16:
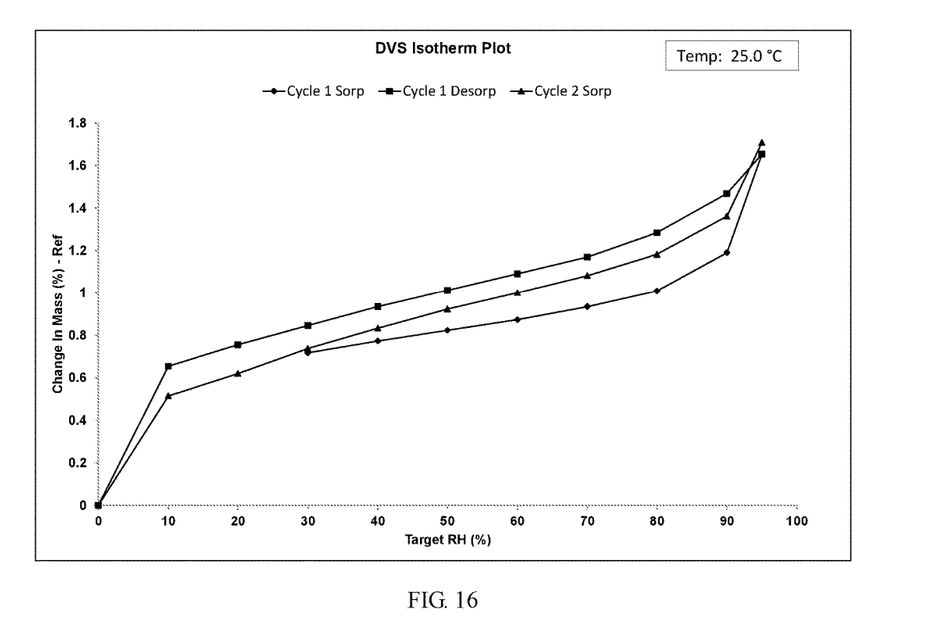
FIG. 16 shows a DVS plot of maleate crystalline Form C

Hygroscopicity of 10 mg of Form C of the present invention was tested using dynamic vapor sorption (DVS) at 25° C. The result is listed in Table. 9. The DVS isotherm plot is shown in FIG. 16.

TABLE 9

| Solid Form | weight increment under 80% Relative Humidity |
|---|---|
| Form C | 1.01% |

About hygroscopicity characterization description and definition of hygroscopicity (Chinese Pharmacopoeia 2010 edition appendix XIXJ Drug hygroscopic test guidelines, test at 25° C.+/−1° C., 80% Relative Humidity)

deliquescent: sufficient water is absorbed to form a liquid;

very hygroscopic: increase in mass is equal to or greater than 15 percent;

hygroscopic: increase in mass is less than 15 percent and equal to or greater than 2 percent;

slightly hygroscopic: increase in mass is less than 2 percent and equal to or greater than 0.2 percent.

no or almost no hygroscopic: increase in mass is less than 0.2%

The result indicates that the weight increment of maleate crystalline Form C of the present invention is 1.01% when it is placed under 80% RH. The hygroscopicity is quite low, and Form C is suitable for long-term storage. On the other hand, due to the low hygroscopicity of the crystalline form, the preparation and post-treatment process is simple. And it is easy for the commercial production. Since moisture content of the crystalline form remained unchanged under different humidity conditions. There is no special requirement on the storage conditions. The cost of materials storage and quality control will be greatly reduced, with strong economic value.

EXAMPLE 10

Stability comparison of maleate crystalline Form C in the present invention and maleate crystalline Form II in CN101918390B:

10.0 mg of maleate crystalline Form C and maleate crystalline Form II in CN101918390B were mixed at a ratio of 1:1 and added into 1.0 mL of solvent to obtain a suspension. The suspension was magnetically stirred at 500 rpm at 25° C. for 24 hours, and centrifuged to give a solid which was tested by XRPD. The result is listed in Table 10.

TABLE 10

| No. | temperature | solvent | Initial form | Stirring time | Final form |
|---|---|---|---|---|---|
| 1 | 5° C. | nitromethane | Form C and Form II in CN101918390B | 24 hours | Form C |
| 2 | 25° C. | nitromethane | Form C and Form II in CN101918390B | 24 hours | Form C |

The result shows that maleate crystalline Form II in CN101918390B transferred to crystalline Form C of the present invention. Form C of the present invention is more stable than maleate crystalline Form II of in CN101918390B.

EXAMPLE 11

Stability assessment of Form C of maleate of the compound of Formula (I)

Figure 17:
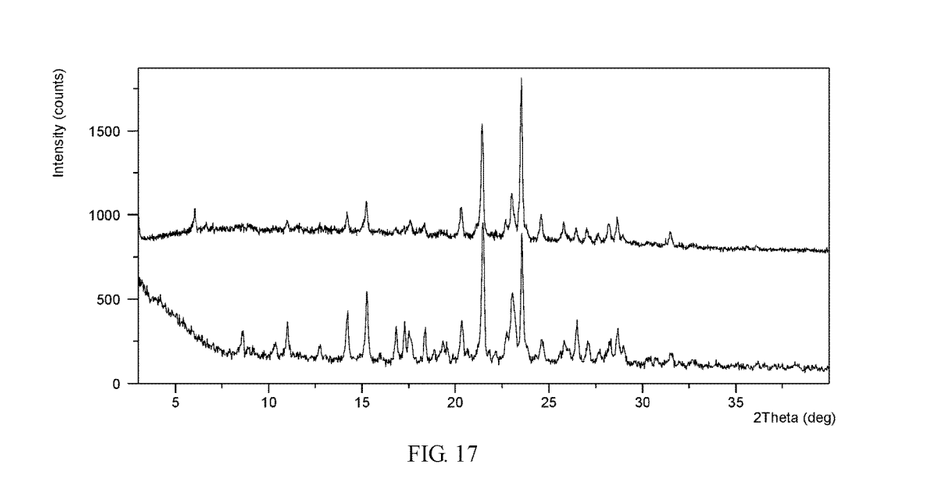
FIG. 17 shows an XRPD overlay pattern of maleate crystalline Form C before and after storing at 5° C. for 330 days (the pattern above is before storing and the below one is after storing)
Figure 18:
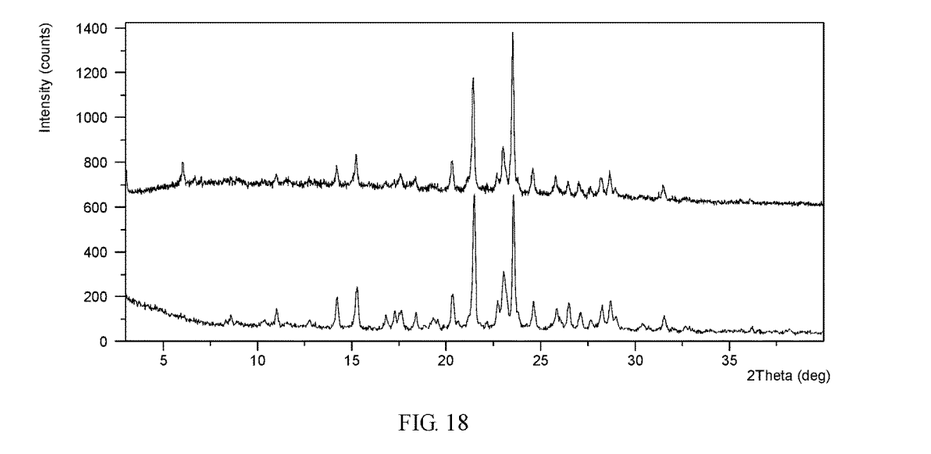
FIG. 18 shows an XRPD overlay pattern of maleate crystalline Form C before and after storing at 25° C./60% RH for 330 days (the pattern above is before storing and the below one is after storing)
Figure 19:
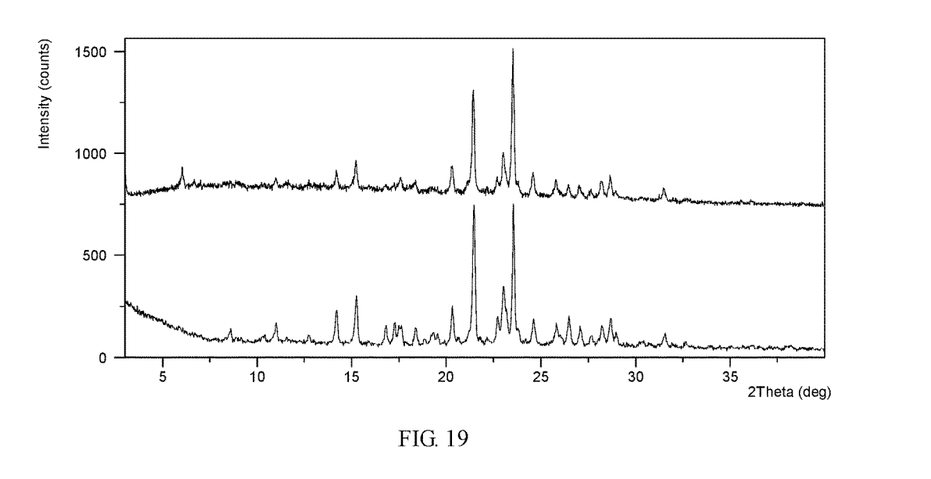
FIG. 19 shows an XRPD overlay pattern of maleate crystalline Form C before and after storing at 40° C./75% RH for 330 days (the pattern above is before storing and the below one is after storing)

Form C of the present invention was stored under 5° C., 25° C./60% RH and 40° C./75% relative humidity for 330 days. XRPD patterns were collected after storage. The experiment result is shown in Table 11. The XRPD patterns of Form C before and after storing under the three stress conditions for 330 days are displayed in FIG. 17, FIG. 18 and FIG. 19 (the patterns above in FIG. 17, FIG. 18 and FIG. 19 were the XRPD patterns of Form C before storing).

TABLE 11

| Initial Form | conditions | Storage time | Form Change |
|---|---|---|---|
| Form C | 5° C. | 330 days | Form C doesn't change (FIG. 17 below) |
|  | 25° C./60% RH | 330 days | Form C doesn't change (FIG. 18 below) |
|  | 40° C./75% RH | 330 days | Form C doesn't change (FIG. 19 below) |

The result indicates that maleate crystalline Form C of the compound of Formula (I) remains unchanged under 5° C., 25° C./60% RH and 40° C./75% RH for 330 days. The maleate crystalline Form C of the compound of Formula (I) has good stability.

EXAMPLE 12

Solubility comparison study between crystalline forms of maleate of the present invention and crystalline Form II in CN101918390B.

Maleate crystalline Form A, Form B of the present invention and maleate Form II in CN101918390B were added in pH 1.8 SGF (simulated gastric fluid), and in high purity water to obtain suspensions. Concentrations in the saturation solutions were determined after 1 hour, 4 hours and 24 hours by HPLC. The result is listed in Table 12.

TABLE 12

| Time point (h) | pH 1.8 SGF | | | H₂O | | |
|---|---|---|---|---|---|---|
| | Form II | Form A | Form B | Form II | Form A | Form B |
| Solubility (mg/mL) 1 | 3.3 | >8.4 | >6.7 | 1.0 | >3.9 | >5.4 |
| 4 | 3.2 | >8.4 | >6.7 | 0.94 | >3.9 | >5.4 |
| 24 | 3.1 | >8.4 | >6.7 | 0.94 | >3.9 | >5.4 |

The comparison results suggest that maleate crystalline Form A, or Form B of the present invention have higher solubility in pH 1.8 SGF (simulated gastric fluid) and in high purity water after 1 hour, 4 hours and 24 hours in comparison to maleate Form II in CN101918390B.

What is claimed is:

1. A maleate crystalline Form C of the compound of Formula (I), wherein the X-ray powder diffraction pattern shows characteristic peaks at 2theta values of 10.9±0.2°, 15.2°±0.2° and 23.5°±0.2°

(I)

2. The maleate crystalline Form C of the compound of Formula (I) according to claim 1, wherein the X-ray powder diffraction pattern further shows one or more of the characteristic peaks at 2theta values of 14.2±0.2°, 21.4°±0.2°, 24.5°±0.2°, 23.0°±0.2°, 18.2°±0.2° and 20.3°±0.2°.

3. The maleate crystalline Form C of the compound of Formula (I) according to claim 1, wherein the X-ray powder diffraction pattern is substantially as depicted in FIG. 7.

4. A process of preparing maleate crystalline Form C according to claim 1, wherein the process comprises: adding the compound of Formula (I) and maleic acid into one or more nitro-hydrocarbon solvents, then stirring to get crystals; or stirring the amorphous maleate salt of Formula (I) in one or more halogenated hydrocarbon solvents, then stirring to get crystals.

5. The process of preparing maleate crystalline Form C according to claim 4, wherein the halogenated hydrocarbon solvents is dichloromethane and the nitro-hydrocarbon solvent is nitromethane.

6. The process of preparing maleate crystalline Form C according to claim 4, wherein the molar ratio of the compound of Formula (I) and maleic acid is from 1:1 to 1:1.5.

7. A pharmaceutical composition comprising maleate crystalline Form C according to claim 1 and pharmaceutically acceptable excipients.

8. A method of treating, or inhibiting cancer, comprising administering the maleate crystalline Form C according to claim 1.

9. A tri-maleate crystalline Form A of compound of Formula (I), wherein the X-ray powder diffraction pattern shows characteristic peaks at 2theta values of 5.1°±0.2°, 6.9°±0.2°, 11.4°±0.2°, and 13.9°±0.2°

(I)

10. The tri-maleate crystalline Form A of compound of Formula (I) according to claim 9, wherein the X-ray powder diffraction pattern further shows one or more of the characteristic peaks at 2theta values of 18.3°±0.2°, 13.2°±0.2°, 15.2°±0.2°, 21.6°±0.2° and 22.5°±0.2°.

11. The tri-maleate crystalline Form A of compound of Formula (I) according to claim 9, wherein the X-ray powder diffraction pattern is substantially as shown in FIG. 1.

12. The tri-maleate crystalline Form A of compound of Formula (I) according to claim 9, wherein crystalline Form A is an anhydrate.

13. A process of preparing tri-maleate crystalline Form A according to claim 9, wherein the process comprises: adding the compound of Formula (I) and maleic acid into one or more organic solvents selected from ketone solvents, alcohol solvents and halogenated hydrocarbon solvents, then stirring to get crystals.

14. The process of preparing tri-maleate crystalline Form A according to claim 13, wherein the organic solvent is selected from acetone, isopropanol and dichloromethane.

15. The process of preparing tri-maleate crystalline Form A according to claim 13, wherein the molar ratio of the compound of Formula (I) and maleic acid is between 1:2 to 1:5.

16. A pharmaceutical composition, comprising an effective amount of tri-maleate crystalline Form A according to claim 9 and pharmaceutically acceptable excipients.

17. A method of treating, or inhibiting cancer, comprising administering the tri-maleate crystalline Form A according to claim 9.

18. A tri-maleate crystalline Form B of the compound of Formula (I), wherein the X-ray powder diffraction pattern shows characteristic peaks at 2theta values of 5.4°±0.2°, 13.5°±0.2° and 19.6°±0.2°

(I)

19. The tri-maleate crystalline Form B of the compound of Formula (I) according to claim 18, wherein the X-ray powder diffraction pattern further shows one or more of the characteristic peaks at 2theta values of 10.7±0.2, 12.1°±0.2°, 23.8°±0.2°, 9.9°±0.2°, 22.2°±0.2° and 17.6°±0.2°.

20. The tri-maleate crystalline Form B of the compound of Formula (I) according to claim 18, wherein the X-ray powder diffraction pattern is substantially as shown in FIG. 4.

21. The tri-maleate crystalline Form B of the compound of Formula (I) according to claim 16, wherein the crystalline Form B is a hydrate.

22. A process of preparing tri-maleate crystalline Form B of the compound of Formula (I) according to claim 18, wherein the process comprises: stirring tri-maleate crystalline Form A in water or placing tri-maleate crystalline Form A at 60% or above humidity conditions.

23. A pharmaceutical composition, comprising tri-maleate crystalline Form B according to claim 18 and pharmaceutically acceptable excipients.

24. A method of treating, or inhibiting cancer, comprising administering the tri-maleate crystalline Form B according to claim 18.

25. A pharmaceutical composition comprising effective amount of tri-maleate crystalline Form A of the compound of Formula (I) according to claim 9, tri-maleate crystalline Form B of the compound of Formula (I) according to claim 18, maleate crystalline Form C of the compound of Formula (I) according to claim 1, or a combination thereof and pharmaceutically acceptable excipients.

* * * * *